United States Patent [19]

Nadel

[11] Patent Number: 5,788,648

[45] Date of Patent: Aug. 4, 1998

[54] ELECTROENCEPHALOGRAPHIC APPARATUS FOR EXPLORING RESPONSES TO QUANTIFIED STIMULI

[75] Inventor: Eric Tab Nadel, Miami, Fla.

[73] Assignee: Quantum Interference Devices, Inc., Miami, Fla.

[21] Appl. No.: 812,115

[22] Filed: Mar. 4, 1997

[51] Int. Cl.$^6$ ........................................ A61B 5/04
[52] U.S. Cl. ........................ 600/544; 600/545; 600/546; 600/300
[58] Field of Search ........................ 600/544, 545, 600/546, 300

[56] References Cited

U.S. PATENT DOCUMENTS

| | | |
|---|---|---|
| Re. 34,015 | 8/1992 | Duffy .................................. 600/544 |
| 3,773,049 | 11/1973 | Rabichev et al. . |
| 3,780,724 | 12/1973 | John .................................. 600/544 |
| 3,880,144 | 4/1975 | Coursin et al. ...................... 600/544 |
| 3,893,450 | 7/1975 | Ertl .................................... 600/544 |
| 4,013,068 | 3/1977 | Settle et al. . |
| 4,201,224 | 5/1980 | John .................................. 600/544 |
| 4,216,781 | 8/1980 | John .................................. 600/544 |
| 5,123,899 | 6/1992 | Gall . |
| 5,213,562 | 5/1993 | Monroe . |
| 5,356,368 | 10/1994 | Monroe . |
| 5,394,164 | 2/1995 | Gandhi et al. . |
| 5,617,871 | 4/1997 | Burrows ............................. 600/300 |

*Primary Examiner*—Jennifer Bahr
*Assistant Examiner*—Stephen Huang
*Attorney, Agent, or Firm*—Oltman, Flynn & Kubler

[57] ABSTRACT

An electroencephalographic apparatus for exploring a person's response to external stimuli, which includes electroencephalographic sensing apparatus for sensing brainwave signals from the person; stimulating apparatus for generating the stimuli; and processing apparatus having at least a first input operative for receiving the brainwave signals, at least a second input for monitoring the stimuli; the processing apparatus including computing apparatus operative for computing a correlation quotient of the brainwave signals and the stimuli.

8 Claims, 4 Drawing Sheets

ELECTROENCEPHALOGRAPHIC APPARATUS FOR EXPLORING RESPONSES TO QUANTIFIED STIMULI

The invention relates to electroencephalographic apparatus aimed at exploring a person's reactions and responses as expressed in the person's brainwave signals in response to various external quantifiable stimuli. In particular the invention is directed to generating such responses in quantified format and to generate correlation coefficients between the stimuli and the responses.

BACKGROUND OF THE INVENTION

A considerable amount of research has been undertaken in exploring the nature and significance of human brainwaves, as they can be studied by sensitive electronic sensing devices.

Encephalographic devices are described in U.S. Pat. No. 4,013,068, which relates to an encephalographic activated control system, U.S. Pat. No. 5,356,368, which describes methods and apparatus for entraining human brain patterns by means of frequency following response techniques. In this reference, in one embodiment, a plurality of electroencephalographic wave forms characteristic of a given state of consciousness, are combined to yield an electroencephalographic waveform to which subjects may be susceptible. U.S. Pat. No. 5,123,899 shows examples of different brainwaves.

From the prior art it is known that human brain wave signals can be resolved into so-called alpha-waves, beta-waves, delta-waves and so forth, and that each react differently in response to external stimuli, such as light, sounds, smells, tactile stimuli, etc.

Applicant, however, is unaware of earlier explorations directed to the object of correlating quantitatively any connection between external stimuli and the brainwave responses of a human brain. In this context the range of interest is especially directed to the domain of quantifying a relation between various phases of external stimuli and resulting brain waves, but not limited to responses to quantifiable stimuli that can be expressed and measured quantitatively.

The invention is by extension also directed to the domain of quantifying a so-called auto-correlation between various phases of application of external stimuli.

SUMMARY OF THE INVENTION

The invention is directed to the art of expanding the art of exploring and analyzing a person's responses to stimuli, i.e. stimulations applied in the form of quantifiable stimuli including, but not limited to, external stimuli in the form of any one of and combinations of oral, visual, tactile, acoustic and/or olfactory stimuli. In accordance with the invention, there is provided electroencephalographic apparatus for exploring a person's response to external stimuli, which includes electroencephalographic sensing apparatus for sensing brainwave signals from the person; stimulating apparatus for generating the stimuli; and processing apparatus having at least a first input operative for receiving the brainwave signals, at least a second input for monitoring the stimuli; the processing apparatus including computing apparatus operative for computing a correlation quotient of the brainwave signals and the stimuli.

According to a further feature of the invention the electroencephalographic sensing apparatus includes brainwave signal sensing apparatus coupled to the person's brain, and amplifying apparatus coupled to the brainwave signal sensing apparatus for amplifying and conditioning the brainwaves for entry to the processing apparatus.

According to another feature, the apparatus according to the invention includes stimulating apparatus having quantizing apparatus for quantizing the stimuli, wherein further the stimuli include at least one of visual, oral, tactile, acoustic and olfactory stimuli.

According to an additional feature, the quantizing apparatus includes a quantifier having an output coupled to the processing apparatus, wherein the processing apparatus includes a microprocessor, and a memory coupled to the processor for storing processing programs for the microprocessor.

Again, according to another feature a Fourier algorithm is stored in the memory for transforming the brainwave signal into a Fourier signal, wherein the Fourier algorithm can be a fast Fourier algorithm.

According to a still further feature, the apparatus according to the invention provides a correlation transform stored in the memory for generating a correlation coefficient between the brainwave signal and the stimuli.

The apparatus according to the invention may further include an encryption algorithm stored in the memory for encrypting the correlation coefficient.

In the inventive apparatus, the brainwave signal can be divided into phases including an early phase before receipt of the stimuli, and a later phase following the stimuli, and the correlation transform algorithm may be operative for generating an auto-correlation coefficient based on the correlation between the early and the later phases.

The invention may further include data transmission apparatus for transmitting the correlation factor to a receiving entity spaced apart from the processing apparatus, and a data base in the memory for storing computing data for the microprocessor.

Further objects and advantages of this invention will be apparent from the following detailed description of a presently preferred embodiment which is illustrated schematically in the accompanying drawings.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

DESCRIPTION OF THE PREFERRED EMBODIMENTS

Figure 1:
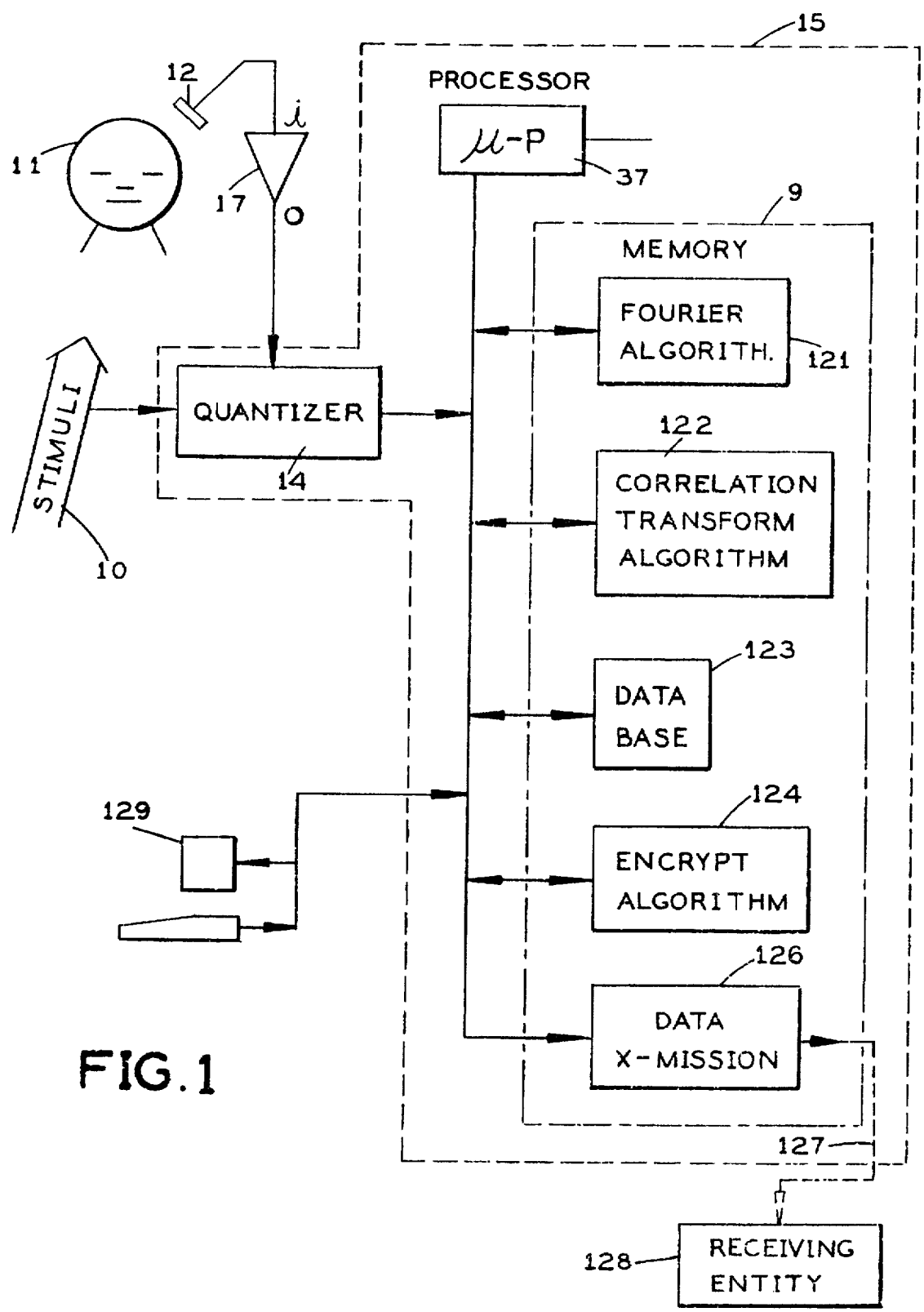
FIG. 1 is a basic block-diagram of the invention, broadly presented.

In FIG. 1 a person 11 is coupled to an electroencephalographic processing arrangement 15 via a sensing apparatus 12, which can have different forms, e.g. as a sensing plate 12 disposed in close proximity to the brain of the person. The sensing device can have other forms, such as e.g. one or more electrodes 13 (FIG. 2) held in close contact with the head of the person 11. The output of the sensing device is coupled to an input of a sensitive preamplifier 17 having an output O connected to the processor 15. A stimulating arrangement shown here simply as an arrow 10 is arranged to apply one or more stimuli to the person. The stimuli can preferably be of a quantifiable type which can be measured and recorded numerically. Examples of stimuli are visual displays or light signals of different colors and intensities, oral instructions presented in a quantifiable manner which operate to make different impressions on the person 11, or tactile stimuli such as pressure applied in different magnitudes to some part of the person, or acoustic sounds which can be applied in different frequencies or intensities or olfactory stimuli which can be applied in the form of different types of smell of different intensities. A quantizing device, including essentially an analog measuring device connected to an analog to digital converter (A/D converter) measures and quantifies the stimuli and presents its digital output to the processor 15, in addition to the brainwave signal. In the processor 15 both the stimuli and the brainwave signals are processed through a Fourier transform 121, the algorithm for which is stored in memory (i.e. data base 123 of the processor. After being processed through the Fourier transform, the respective elements of the transform are processed in a correlation quotient transform algorithm 122, also stored in memory in the processor 15. The correlation coefficient produced by the correlation transform algorithm is a measure for the degree of correlation between the stimuli and the brainwave signals.

Descriptions of Fourier transforms and correlation algorithms are well known and widely described in engineering and mathematical literature and have therefore not been described in detail in this disclosure.

The resulting correlation coefficient may be stored in the processor's data base and used for further research, or displayed on an output device 128. Alternatively the results may be transmitted via a data transmission device 126 to a remote receiving entity 128, such as e.g. research center or the like.

Due to the potentially sensitive nature of such highly personal information, the data may be processed through an encryption algorithm 124, also stored in the data base 123 of the processor.

Figure 2:
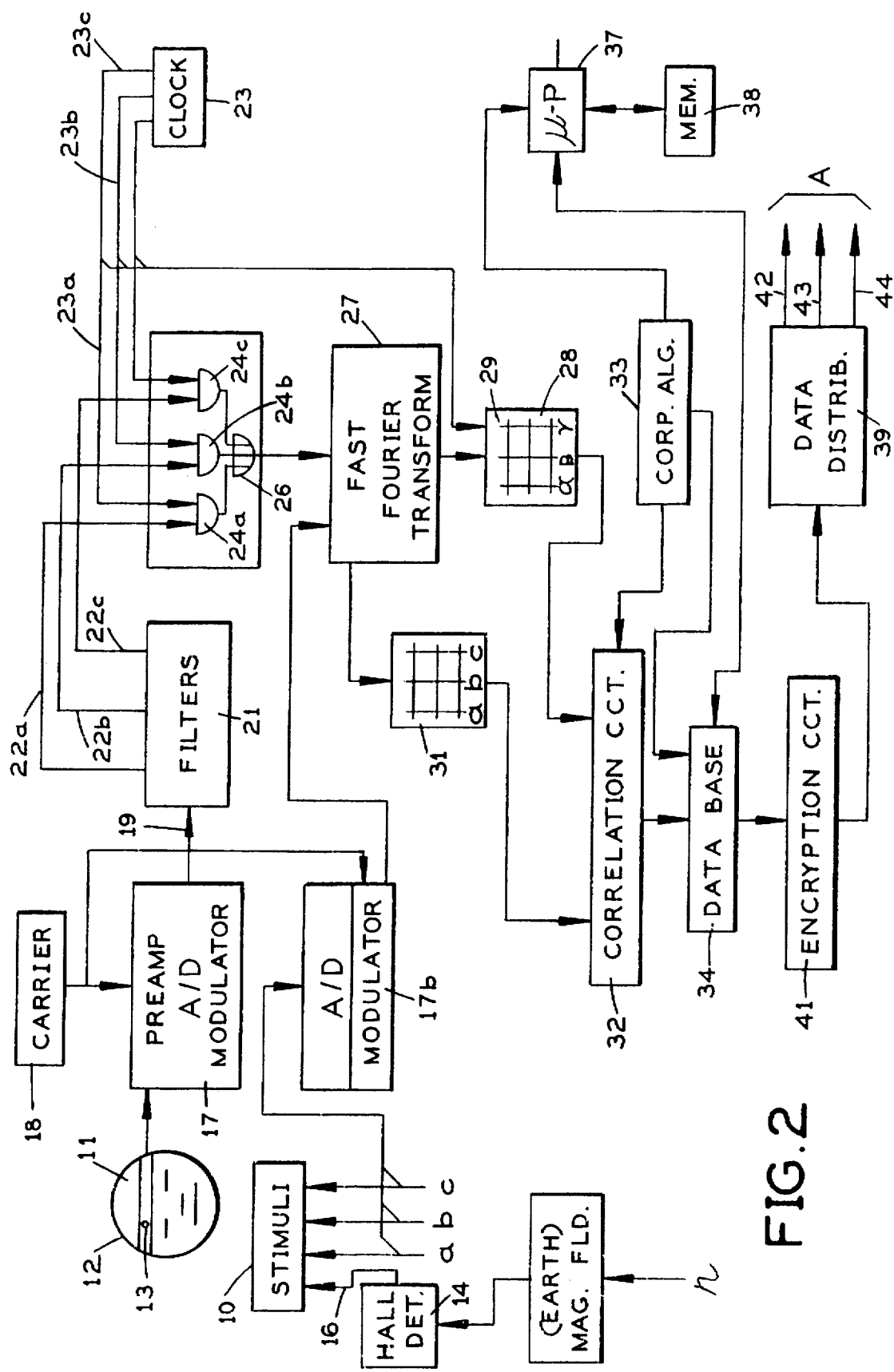
FIG. 2 is a more detailed block-diagram showing details of the electronic response and an analysis system.

FIG. 2 shows a more detailed block diagram of the processor 15. In FIG. 2 various stimuli are entered at respective inputs a,b,c, etc. of a stimuli pre-processing circuit 10.

In FIG. 2 the person 11 is equipped with an electrode or set of electrodes 12 as conventionally used in electroencephalic explorations. The electrode 12 may include a plurality of encephalographic electrode units 13 each of which may be selected, or selected in combinations of electrode units 13. The electrode units 13 may be selected by a selection device not shown. The person 11 can be exposed to a plurality of stimuli a,b,c,–n presented singly or in combination. The stimuli are typically in the nature of visual, oral, tactile, acoustic, olfactory stimuli, but may further include impressions such as electric, magnetic, temperature induced sensations and so forth. Magnetic impressions are measured by a Hall detector 14 which has an electric output 16. The brainwaves as detected by electrode units 12 are amplified in an A/D converter and preamplifier-modulator circuit 17 which preamplifies the brain signals and transposes the frequency of the signals to a higher frequency by means of a carrier signal generator 18, and appear as a transposed higher frequency input at 19 of a set of frequency band filters 21, causing discrete signal frequencies to appear at filter outputs 22a, 22b, 22c, etc. The discrete signal frequencies are scanned by a clock 23 having corresponding clock output signals of different phases 23a, 23b, 23c, etc. applied to a set of scanning gates 24a, 24b, 24c, etc. The outputs of the scanning gates are combined in an OR-gate 26 and applied sequentially to a fast Fourier transform circuit 27, which resolves the individual brain waves as applied to a recirculating memory matrix 28. Each of a plurality of crosspoints of matrix 28 represents a memory cell 29. The vertical columns of memory cells 29 represent the momentary amplitude of constants of the Fourier transforms of the individual brainwaves alpha, beta, gamma delta, etc. which are stored momentarily at vertical crosspoints, alpha, beta, gamma, delta, etc.. At the same time the stimuli a,b,c are resolved in respective harmonics in another recirculating memory matrix 31 having verticals a,b,c corresponding to verticals alpha, beta, gamma, delta, etc. of matrix 28.

A correlation circuit 32 computes, by means of a correlation algorithm stored in correlation algorithm circuit 33, the cross-correlation coefficients between each brainwave signal alpha, beta, gamma, . . . and the respective stimuli a,b,c . . . etc.

It follows that other correlations may be of interest, such as correlations between values stored in verticals a,b,c and alpha and beta, and so forth. Furthermore, auto-correlations between different phases of signals alpha, beta, gamma, etc. may be of interest. Various correlations may be selected from a manual keyboard 33 controlling the correlation circuit 32.

The resulting correlations may be stored in a database 34 under control of a micro-processor (μp) (37) connected to a program memory 38. The data in database 34 may be distributed to interested and/or authorized entities or agencies A, via a data distribution circuit 39. Due to the potentially sensitive nature of the data, an encryption circuit 41 may be interposed between distribution circuit 39 and the data base 34.

The data distribution circuit 39 is capable of transmitting the encrypted data on any one of a number of transmission channels 42, 43, 44, which may be conventional or dedicated voice band data channels, and which may employ any type of data transmission media such as cable, fiber-optic, microwave, etc., or packet-switched data channels.

Figure 3:
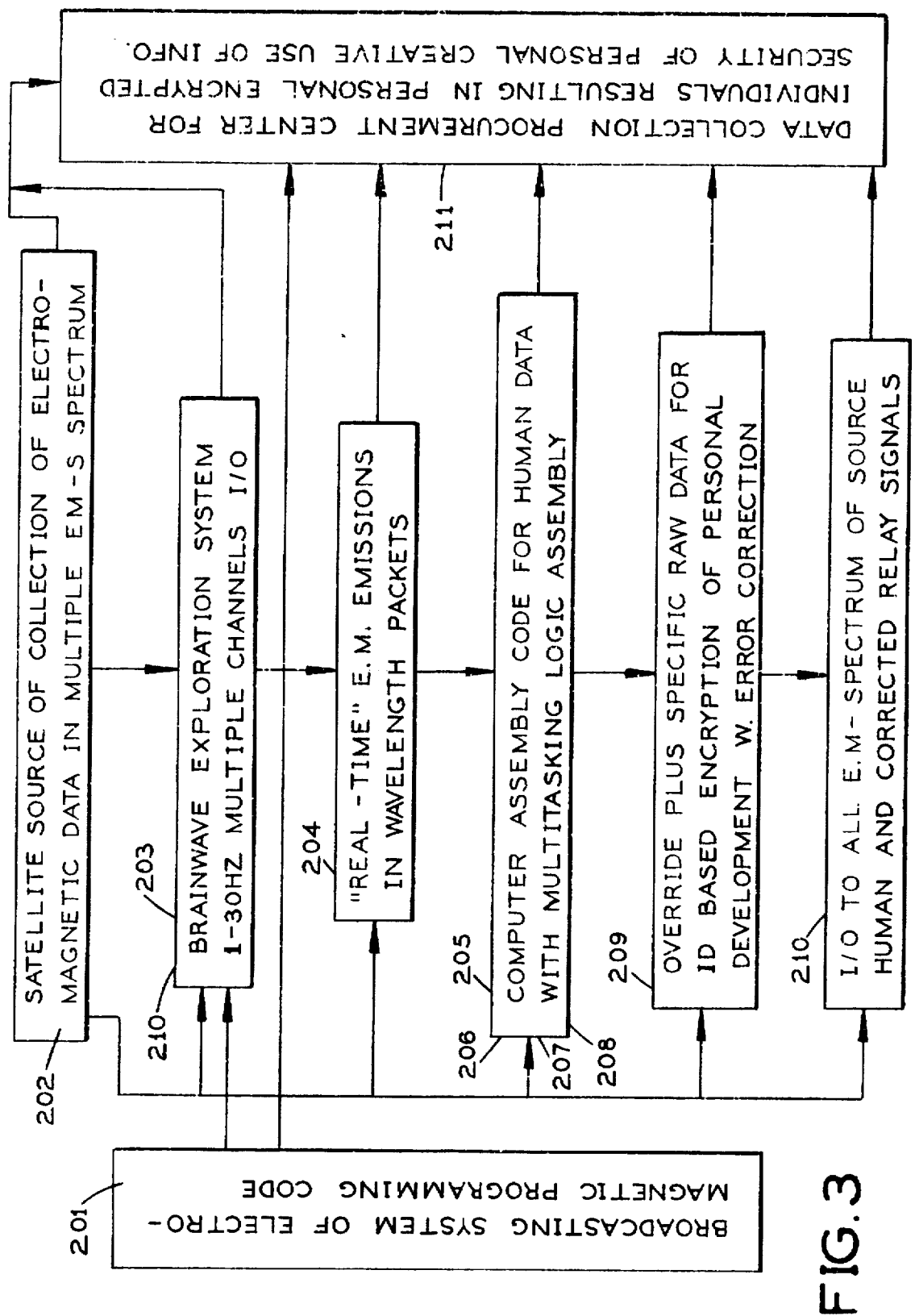
FIG. 3 is a block-diagram of a broadly presented advanced layout of the invention.

FIG. 3 shows a contemplated expanded version of the invention for further exploration of brain-wave signals, wherein a satellite source for collection of electromagnetic data in multiple electromagnetic spectra 202 feeds the data to a brainwave exploration system in the 1–30 HZ range via multi-channel I/O 210, 203, or via "real-time" electromagnetic emissions in wavelength packets (204) to a data collection procurement center 211 for individuals resulting in personal encrypted security I.D. of personal creative use of information.

The satellite source of collection 202 further communicates with a repository 205 (207, 206, and 208) for human data with multi-tasking logic assembly, and with an override facility 209 plus specific raw data for ID based encryption of personal development with error correction, and with an I/O feature 210 to all EM-spectrum of source human and corrected relay signals. The features of brainwave exploration system 210, 203, the real-time E.N. emissions 204, the computer assembly code 205 (207, 206, and 208), the override plus specific raw data 209, and the I/O 210, all present data to a data procurement center 211, for individuals resulting in personal encrypted security of personal creative use of information. Furthermore, a broadcasting system 201 feeds electromagnetic programming code to the brainwave exploration system 210 (203).

Figure 4:
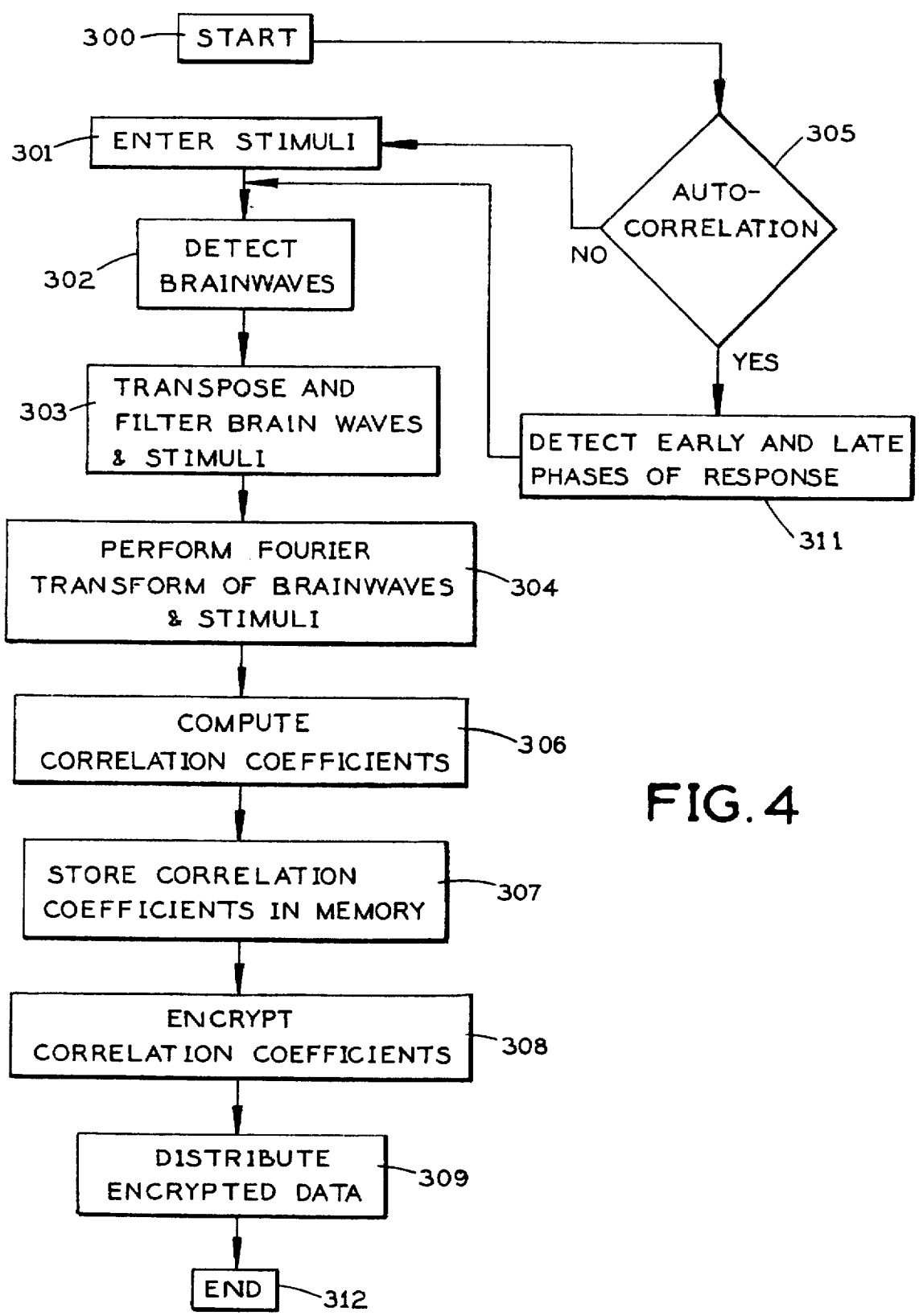
FIG. 4 is a flow chart showing major program steps of the control arrangement.

FIG. 4 is a flow-chart showing the steps of processing the correlation between stimuli and brainwave responses. In start step 300, a decision step 305 determines whether a correlation between stimuli and responses is to be performed from the NO output or an auto-correlation between subsequent phases of the output response is to be determined from the YES output. If the decision is NO, external stimuli are entered at step 301, followed by a frequency transposition of the brain waves and the stimuli to a higher frequency which will facilitate the following signal processing steps. In step 304 a Fourier transformation is performed on the brainwaves and the stimuli. The Fourier transforms of these signals is represented by respective series of Fourier coefficients that are computed by the Fourier integrals:

$$a_n = \int_{-\pi}^{\pi} f(x)\cos nx\, dx \quad (n = 0, 1, 2, \ldots)$$

$$b_n = \int_{-\pi}^{\pi} f(x)\sin nx\, dx \quad (n = 1, 2, 3, \ldots)$$

The correlation coefficient, usually designated by r, is computed in step 306 by the equation:

$$r = \frac{\sum_{t=1}^{n}(x_t - x)(y_t - y)}{\sqrt{\sum_{t=1}^{n}(x_t - x)^2 \cdot \sum_{t=1}^{n}(y_t - y)^2}}$$

The resulting correlation coefficients as continuously computed are stored in memory in step 307 and, if necessary, encrypted in step 308, and outputted and distributed in step 309. If auto correlations are to be evaluated, it starts with output YES in decision step 305, followed by sensing subsequent early and late phase of the brainwaves, e.g. before and after application of stimuli, which in this case need not be quantifiable. Next, auto-correlations are evaluated in steps 302 . . . 309 as described above.

I claim:

1. Electroencephalographic apparatus for exploring a person's response to external stimuli, comprising:

electroencephalographic sensing means for sensing brainwave signals from the person;

stimulating means for generating the stimuli;

processing means having at least a first input operative for receiving said brainwave signals, at least a second input for monitoring said stimuli; said processing means including computing means operative for computing a correlation quotient of said brainwave signals and said stimuli, said processing means including a microprocessor, and a memory coupled to said processor for storing processing programs for said microprocessor;

a Fourier algorithm stored in the memory for transforming said brainwave signals into Fourier signals, said Fourier algorithm being a fast Fourier algorithm;

further including a correlation quotient transform stored in said memory for generating a correlation coefficient between said brainwave signals and said stimuli; and an encryption algorithm stored in said memory for encrypting said correlation coefficient.

2. Apparatus according to claim 1, wherein said electroencephalographic sensing means include brainwave signals sensing means coupled to the person's brain, amplifying means coupled to said brainwave signals, and means for amplifying and conditioning said brainwaves for entry to said processing means.

3. Apparatus according to claim 1, wherein said stimulating means include quantizing means for quantizing said stimuli.

4. Apparatus according to claim 3, wherein said stimuli include at least one of visual, oral, tactile, acoustic and olfactory stimuli.

5. Apparatus according to claim 4, wherein said quantizing means include a quantifier having an output coupled to said processing means.

6. Apparatus according to claim 1, wherein said brainwave signals is divided into phases including an early phase before receipt of said stimuli, and a later phase following said stimuli, and wherein said correlation transform algorithm is operative for generating an auto-correlation coefficient based on said correlation between said early and said later phase.

7. Apparatus according to claim 1, further including data transmission means for transmitting said correlation factor to a receiving entity spaced apart from said processing means.

8. Apparatus according to claim 1, including a data base in said memory for storing computing data for said microprocessor.

\* \* \* \* \*